United States Patent [19]

Halligan et al.

[11] 4,140,583
[45] Feb. 20, 1979

[54] PROCESSING OF LIGNITE FOR PETROCHEMICALS

[75] Inventors: James E. Halligan; William J. Huffman, both of Lubbock, Tex.

[73] Assignee: Pioneer Corporation, Amarillo, Tex.

[21] Appl. No.: 739,269

[22] Filed: Nov. 5, 1976

[51] Int. Cl.² ............................................. C10B 49/06
[52] U.S. Cl. ........................................ 201/4; 48/206; 201/34; 201/38; 208/8
[58] Field of Search ...................... 201/3, 4, 34, 36, 37, 201/38; 208/8; 48/197 R, 202, 203, 206

[56] References Cited

U.S. PATENT DOCUMENTS

| 2,026,923 | 1/1936 | Warner | 201/34 X |
| 2,623,011 | 12/1952 | Wells | 201/34 X |
| 2,879,208 | 3/1959 | Brice | 201/37 X |
| 3,111,395 | 11/1963 | Sweeney | 208/8 X |
| 3,841,992 | 10/1974 | Jones, Jr. et al. | 201/34 X |

FOREIGN PATENT DOCUMENTS 487983  6/1938  United Kingdom ...................... 201/34

Primary Examiner—Morris O. Wolk
Assistant Examiner—Arnold Turk
Attorney, Agent, or Firm—Ely Silverman

[57] ABSTRACT

Process and apparatus for producing ethylene from lignite and subbituminous coal by chemical condition and temperature control using cellulosic material within the treated mass or added thereto whereby ethylene gas is evolved from such carbonacous feed and recovered with other products.

9 Claims, 4 Drawing Figures

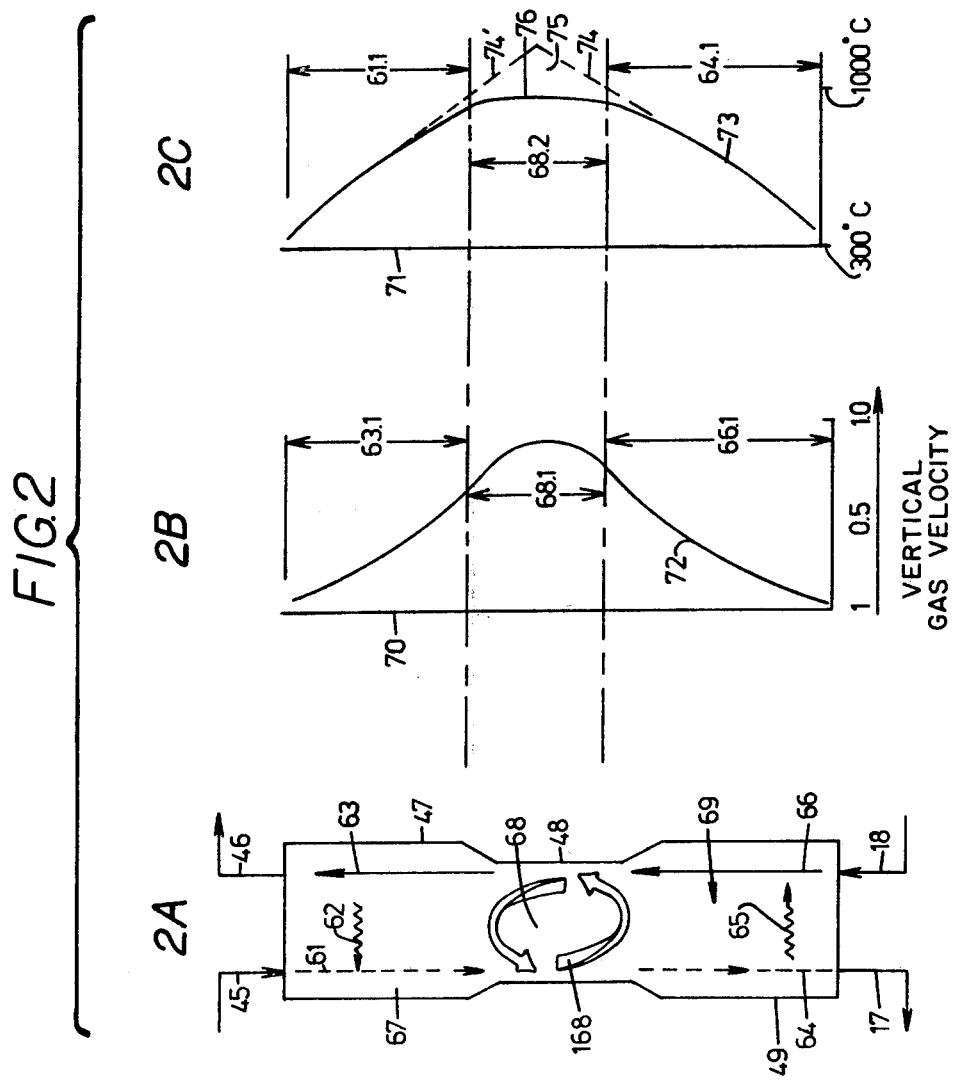

PROCESSING OF LIGNITE FOR PETROCHEMICALS

BACKGROUND OF THE INVENTION

1. Field of the Invention

The field of art to which this invention pertains is the production of ethylene.

2. Description of the Prior Art

While vast resources of lignite are available, e.g., 10 to 20 billion tons in strip mine depths of 0–200 feet, in the prior art no significant economic benefit was obtained above that associated with direct firing of lignite. In view of the well known combustibility of lignite as well as its hydrogen-absorption characteristics it is surprising that the use of lignite or materials similarly characterized have not been heretofore utilized for ethylene production. By this process substantial amounts of useful petrochemical products and ethylene are obtained from lignite and like compositions.

SUMMARY OF THE INVENTION

One portion of a feedstock of finely ground lignite or other cellulose and modified cellulose-containing naturally occurring and/or synthetic mixture, which feedstock also contains hydrogen-absorbing hydrocarbons, reacts with a mixture of steam and air to produce hot gases which fluidize and heat the remaining portion of that feedstock under controlled physical and chemical conditions to evolve and recover ethylene gas in substantial amounts while also producing a solid char and other useful fluid products.

BRIEF DESCRIPTION OF THE DRAWINGS

FIG. 2 is a composite figure: illustrative of temperature and velocity conditions in the reactor 14 during the process.

FIG. 2A illustrates diagrammatically the internal zones of reactor 14 and qualitatively illustrates the material and heat flows therein.

Figure 1:
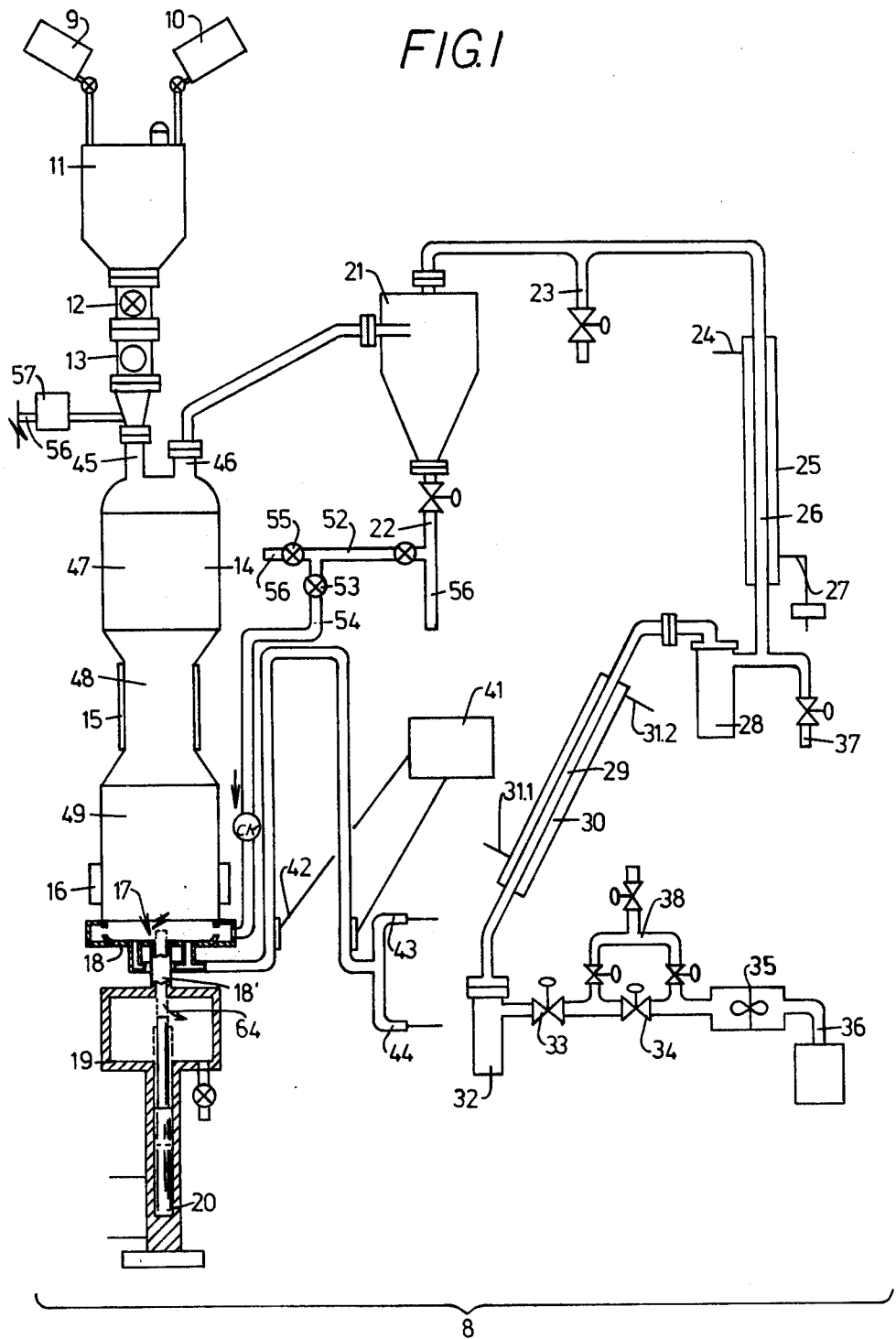
FIG. 1 is a flow diagram of the reactor system.

The vertically extending curved line of FIG. 2B illustrates, by horizontal extension thereon from the vertical axis 60 of FIG. 2B, vertical gas velocities in reactor 14 at vertical positions in reactor 14 corresponding to the vertical positions of points on the curve of FIG. 2B.

The vertically extending curved line of FIG. 2C illustrates, by horizontal extension thereon from the vertical axis 70 of FIG. 2C, temperatures of the reaction mass in reactor 14 at the vertical positions in the reactor 14 corresponding to vertical positions of points on the curve of FIG. 2C. The vertical positions on the vertical axes 60 and 70 are drawn to the same scale as and correspond to the vertical position of location in the reactor 14 along the length of the reactor as shown in FIG. 2A.

DESCRIPTION OF THE PREFERRED EMBODIMENTS

A feed stock of Texas lignite the contents of which are shown in Table I hereto is used in the below described apparatus and process.

The reactor system 8 comprises a first solids feeder 9 and a second solids feeder 10 arranged to discharge contents thereof to a blender and solid feed holder 11. The solid feed holder 11 is operatively connected to and is located on top of star feeder 12. The star feeder 12 connects through a sight glass section 13 to an upper reactor inlet opening 45. Reactor 14 comprises a heater 15, an upper wide reaction chamber portion 47, a middle narrow reaction chamber 48 and a lower wide reaction chamber portion 49; it has an upper solid feed inlet, 45, operatively connected to the top of the reaction chamber portion, 47, a lower gas inlet opening plate, 18, and a lower center solids outlet, 17, operatively attached to the bottom portion of the lower reaction portion 49.

A heater 15 is operatively connected to the middle narrow reaction chamber portion 48 and a heater 16 is operatively connected to the lower reaction chamber portion 49. The solid outlet line 17 connects to a solid collection tank 19: a ram 20 connects to the bottom of the solid collection tank 19 and provides for emptying of that collection tank.

A cyclone 21 is operatively connected to the upper gas outlet 46 of the reactor 14. The lower solids discharge 22 of cyclone 21 provides for solids discharge from the cyclone and the upper cyclone gas outlet line 23 passes into a demister 25 provided with a steam inlet 24 and a steam outlet 27 so that the portion of the product transfer pipe 26 therein is held at a predetermined temperature level intermediate between 212° F. and the product exit temperature from the cyclone 21 whereby tar is removed and collected at tar collector tank 28 while the gas discharge from the tar collection tank 28 passes to a cooled conduit section 29 within a cooling shell 30. That shell 30 is cooled by a water inlet 31.1 which passes through a water outlet 31.2 and provides for condensate formation which condensate is removed at condensate removal tank 32.

A gas outlet of the condensate removal tank is operatively connected to a pressure control valve 33 which is operatively connected to a sample loop 38 and therethrough to a meter 35 and a product gas outlet 36 for collection.

The reactor 14 is constructed from Schedule 40, 316 stainless steel pipe with an average diameter of seven inches and an approximate height of eight feet. The internal diameter of the upper part 47 of the reactor and the lower part 49 have a cross-sectional area which is 1.78 times that of the middle section 48. This diameter increase decreases the fluid velocity and allows some separation of the solid and gas phases in the upper portion. The inlet gas distribution plate 18 of the reactor 14 consists of a ⅜ steel plate with 1/16 inch concentric holes evenly distributed around a 1 inch center port 17 for the discharge of char product.

The lower and middle part of the vessel is heated using 24-inch sections of preformed, electrical heaters as 15 and 16 manufactured by the Lindberg Co. (Model 50752, Type 77-1CSD; temperature limit to 1200° C.). These heaters were used for start-up and steady-state heat demands. Each of the heater sections was rated for 40 amps, 206 volts. An induction preheater 41 is used to heat the input air-stream mixture to 200°–300° C.

Type K thermocouples are used to measure the temperature profile within the reactor and were monitored using a Northrup, 24-point recorder (Model 547). These thermocouples are unshielded and spaced at 6-inch intervals along the entire reactor length. Temperature measurements are also made at key points along the gas separation equipment train for recording on the same multipoint recorder. Reactor temperature is controlled from a wall temperature measurement using silicone controlled-rectifiers to adjust heater input.

Standard equipment is employed downstream to separate entrained solids, organic tars (in liquid form), and water from the gas product, in that sequence. Cyclone 21 is designed using standard procedure using an estimated particle size distribution from a filtered sample. The cyclone 21 was approximately 5 feet high with a diameter of 15 inches and was operated at a 300°–350° C. to prevent condensation of tarry liquid products. This operating temperature permitted a free-flowing solid to be discharged from the cyclone. The rest of the gas separation unit consisted of a commercial demister 25 to condense tar products (100° C. to 150° C.) and a standard double-pipe heat exchanger 30 for removing water (25° C.–100° C.).

In operation of the system 8 according to this process electrical heaters 15 and 16 or part of the low BTU gas-char products collected in earlier cycles of operation are used to initially heat the reactor 14 and make up energy loss or heat transfer to the ambient temperature.

Solid lignite is pulverized so that at least 80% by weight, of such feed has a particle diameter less than 0.15 cm.

Steam is added at inlet 43 in amount of 0.45 lb per lb of lignite MAF (measured as moisture free and ash free) as a fluidizing gas for the lower portion 49 of the reactor, the combustion zone, where total product gas generation is low and passes to the lower reactor inlet plate 18 and provides a gas velocity less than required for fluidization and estimated at 17–20 cm. per second in the particular embodiment herein described.

Air is added at inlet 44 in amount of 0.3 lb per pound of lignite (MAF) to provide oxygen for partial combustion: such amount may be varied to adjust the $N_2:H_2$ ratio as required for sales to an ammonia fertilizer plant, in view of that the water-gas shift reaction would be used in an ammonia plant to convert CO, $CH_4$, and other unrecovered hydrocarbons, as the solid lignite falls countercurrent to the rising feed gas and vapor mixture, heat exchange to the solid occurs which causes the solid components of the lignite to decompose to a product mixture of gas and vaporized or droplet liquids and char: that product mixture adds to the total flow of gas (countercurrent to solid) and increases total gas volume by a multiplicative factor between 1.5 and 2.0.

The pressure control valve 33 is set to maintain a constant pressure of below 7 atmospheres in the reactor 14, usually 5 atmospheres with the quantitative value of the setting of the valve depending on the pressure drop through the system ahead of that valve. Such pressure drop depends on the velocity of gas flow and pressure drops in the components of assembly 8 between the reactor 14 and the pressure control valve; the setting of valve 33 is a procedure well known to those skilled in the art.

The upper reaction zone 67 is located within portion 47 of reactor 14; a narrow middle reaction zone 68 is located in middle reaction chamber portion 48 and lower reaction zone 69 is located in lower wide reaction chamber portion 49.

In zone 68 of maximum gas generation at maximum temperatures as at zone 68.2, the reactor internal diameter is decreased relative to the internal diameter at zones 67 and 69 to effect an increase in gas velocity by a multiplicative factor within a range of 1.5 to 3.0, preferably 2. This increase in gas velocity as at zone 68.1 causes the solid-gas mixture to provide a highly turbulent, intense zone of contact 168 with solids back-mixing to achieve a high degree of conversion of the solid feed to gaseous product and char.

The gas in the column portion 68 is operated at high and constant velocity of 90–180 cm. per sec. and remains in a plug-flow or nearly plug-flow regime with minimized back-mixing of gas at the high temperature used. Thus, gaseous product continues upward as an upper vertically directed stream of hot reducing gases in path 63 toward the solid inlet 45 and outlet 46 at minimum residence time in zone 68.

On either side (zone 67 and in zone 69) of the high temperature-high velocity zone 68 of maximum gas generation, the temperature is lowered as at zones 61.1 and 64.1 and the gas velocity is decreased as at 63.1 and 66.1 to normal fluidization velocities. The reduction in temperature of such gas by heat transfer 62 as at 61.1 in zone 67 while flowing toward the solid inlet helps minimize the potential decomposition of ethylene to $H_2$, C, and $CH_4$. This reduction in velocity also provides sufficient residence time in zone 67 to achieve gas-to-solid heat transfer as at 62 and cooling of the reaction product above the high velocity-high temperature region in zone 68. Below zone 68, in zone 69, the decreased velocity permits the oxidation of char to occur with complete reaction of available oxygen at a sufficiently low temperature (350° to 900° C.) to prevent ash fusion.

The fluid phase products and unreacted input gases exit at the top of the reactor at 46 along with some entrained solids. This fluid product stream is stripped of entrained solids in a cyclone 21 followed by a two-stage condensation at 25 and 30 of tars plus oils and water. The solid-free, dry gas containing 20 to 80 grams of ethylene per 1,000 grams of dry ash free lignite is then sampled at 38 and the flowrate measured at 35. The solid product at 19 is a char which is removed from the bottom of the reactor 14 through a port 17 in the gas distribution plate and stored in a batch hopper 19.

The solids entrained with the upwardly flowing gas stream 63 may be (a) cycled by line 52, open valve 55 and line 56 to be mixed with materials fed at inlet 45 to increase the heat capacity of the stream 61 and so more rapidly reduce the highest temperature of gases exiting from zone 68 or (b) be passed by line 52 and open valve 53 and line 54 to near input opening 18 and, at the increased oxidation potential there met, be burned to increase the proportions of usable char product: the material in line 56 may be passed through a separate cooler 57.

In Zone 69 the hot lignite particles and char produced and made warm in Zone 68 transfer heat to and react with and warm the mixture of air and steam rising (in streams shown as 66 in FIG. 2A) in Zone 69 of reactor 14 and removes substantially all oxygen therefrom so that the hot gas stream meeting the lignite particles in portion 68 of reactor 14 will be a non-oxidizing gas stream.

The lignite particles are composed of substantial portions of cellulosic material interspersed in physically intimate or close association with unsaturated hydrocarbon material that absorbs hydrogen; heating such composite particles in Zone 67 of reactor 14 evolves unsaturated hydrocarbon materials from stream 61 particles while the intimate association of the cellulosic material therein there and in Zone 68 acts to avoid temperature and time peaks that might otherwise accelerate polymerization or pyrolysis of the evolved unsaturated hydrocarbons such as ethylene.

While cellulose in lignite loses fiber structure at 200° C. and becomes amorphous at 250° C., the carbonized cellulose-like material in lignite exhibits such heats of fusion at higher temperatures which heats of fusion serve to stabilize the reaction mass of which it is a part at such higher temperatures. For such purposes, lignites and subbituminous coals containing partially carbonized cellulose with higher fixed carbon percentages than ignite may be used as by adding solid reaction mixture composed of lignite, cellulose, modified cellulose and unsaturated hydrocarbon producing compounds or by adding a solid feed mixture of sub-bituminous coal and solid lignite and unsaturated hydrocarbon-producing compounds in feeder 9 to provide such components to the feed stock in mixer 11 to material deficient in such components as fed by feeder 10 to produce a feed stock material of such relative composition in the reaction zone 68 as to produce the temperature and chemical conditions for stabilization herein discussed for lignite.

Lignite—especially of a given locality and analysis as hereinabove set out—is a well recognized mineral composition so that the condition of the cellulose components thereof may be readily compared with similar components from other feed sources to produce a similar stabilizing influence on the ethylene producing reaction as herein described. For this purpose, blends of material producing this heat exchange stabilization effect maybe synthesized to produce the desired heat stabilization effect herein described in the reaction zone 68 for lignite.

The cellulose content of the lignite, the cellulosic-like carbonized modifications thereof in lignite, and the petrographic structure of the lignite particles all provide a heat of fusion heat exchange capacity that provides for a rapid cooling or quenching of the gases exiting from the hottest reaction zone 68 and so preserve those products by stabilization of those products against pyrolysis and polymerization without hydrogen reduction characteristics that might alter the desired unsaturated compounds as ethylene evolved in zone 67 and 68.

The char product particles which pass into zone 69 from zone 68 are more brittle on their exterior and less brittle on their interior and the exterior portion of such particles acts as an insulator as well as a reaction mass and the interior portions of such particles act as a coolant for the exterior portions thereof. Because the final char particles drawn from exit 17 are the result of a series of reactions that do not all go to completion in the reaction chamber i.e., a non-equilibrium operation exists, their surface/mass ratio, which is determined by the particle diameter, controls the cooling effect in Zone 68 on the gases there evolved. Such interior cooling effects are not reflected by the temperature measurements by surface characteristics as is conventional and as measured here. Thus, although the temperature measured in zone 68 is high, the time there spent by the lignite particles is so short and follows an earlier preheating step at lower temperatures in zone 67 which evolves—in the vicinity of cooler core—some portion of the unsaturates, the unsaturated hydrocarbon components evolved at the high temperature of zone 68 are not destroyed although in a long term equilibrium situations they might be. The presence of the differences in the core and pellicle of the char particle shows a reserve of such heat of fusion providing components in the reaction zone 68.

Also, while the rate of temperature increase in zone 67 of reactor 14 is a substantial and high temperature gradient that is nearly linear, (and it also is in zone 69) as the feedstock temperature changes from ambient temperature (40° C.) to about 900° C., the temperature change in zone 68, as shown in zone 68.2 of FIG. 2C is, relatively, substantially a plateau, i.e., plus or minus 20% in the range of 800°–1000° C., as also shown in FIG. 2C by the difference, 75, in temperature level from (a) dashed extrapolation lines 74 and 74' tangent to line 73 in zone 64.1 and 61.1 and (b) level 76 on line 73 of FIG. 2C.

Also, the gas velocity is at a regulated peak in zone 68. Accordingly, the residence time of the reactant materials in high temperature zone 68 is closely controlled and brief. Thereby, the temperature and pressure of the reaction zone 68 are held to a value too low to hydrogenate unsaturates at the residence time used although high enough for volatilization of unsaturates by virtue of heat transfer (62) to the initially cool mass flow 61 from the upwardly rising hot gas stream 63.

In zone 67 the hot reaction gases of stream 63 are cooled by the inlet stream 61 and are in a reducing atmosphere too weak to hydrogenate unsaturated components released by the stream 61 of lignite particles freshly added to zone 67 and the cellulosic components of the lignite serve as heat absorbents to more rapidly quench the stream 63 and so avoid polymerizing reactions of the unsaturated hydrocarbons released from the lignite particles in reaction zone 68 while the smaller particles of char produced in zone 68 carried upward to zone 67 have a stable reducing and non-oxidizing action but not a hydrogenating one on the unsaturated material released by stream 61.

The products in addition to ethylene include a dry, 8,000 BTU/lb char and synthesis gas ($N_2 + H_2$) and/or a low (300–400 BTU/SCF) gas. These products are used as supplemental feedstocks to the petrochemical, fertilizer, and/or utility industries, as substitutes for premium natural gas that is currently used, and a significant feature of the reactor design is its simplicity. All products (prior to separation as shown in FIG. 1) are produced, solids drying is accomplished, and partial combustion is achieved in a single reactor 14 with no internal moving parts. This design simplicity provides the means for developing a lignite process with minimum investment.

The process is particularly adapatable to the Gulf Coast portion of the United States where established petrochemical and agricultural industries exist, lignite or sub-bituminous reserves have been proven, and natural gas is widely used by utilities.

An analysis of the sub-bituminous coals above referred to for use in this process is set out in Table I.

TABLE I

| PROPERTIES OF FEEDS | | |
|---|---|---|
| | Sub-bituminous (Wyoming) | Texas Lignite |
| Proximate Analysis, % | | |
| Moisture | 16–24 | 30 |
| Volatile Matter | 27–34 | 33–35 |
| Fixed Carbon | 38–40 | 22–29 |
| Ash | 6–7 | 12–13 |
| Ultimate Analysis, % | | |
| Hydrogen | 6.4 | 5–6 |
| Carbon | 55 | 70–73 |
| Nitrogen | 1.0 | 1.5–1.8 |
| Oxygen | 33 | 18–23 |
| Sulfur | 0.4–1.0 | 1–1.5 |
| Ash | 6–8 | 12–13 |
| BTU/lb | 8500 | 7100–7900 |

We claim:

1. Process of operating a reactor container and producing an ethylene containing gas, said reactor container extending vertically and having near its bottom a bottom low gas velocity zone with a fluidizing gas feed to said bottom zone, and an upper low gas velocity zone located adjacent the top of said reactor container and, intermediate said upper and said bottom zones, a middle high gas velocity maximum temperature zone and comprising steps of;

feeding a fluidizing gas feed to said bottom zone;

passing a vertically directed stream of hot reducing gases upwardly through said upper zone in said reactor container, said hot reducing gases coming from the bottom and middle zones of said reactor container; and operating said reactor with (a) a linear and upwardly decreasing temperature gradient gas in said upper zone of said reactor container, (b) a linear and upwardly increasing temperature gradient gas in said bottom zone, and (c) a temperature maintained at a steady value within range of 800°–1,000° C. and a gas velocity maintain at a steady value within range of 90–180 cm. per sec. at pressures less than 7 atmospheres in said middle zone;

adding a solid particulate feed comprising solid lignite and having a chemical analysis as in Table I, said lignite being in form of a ground mass of solid particles 80% by weight less than 0.15 centimeters in diameter, downwardly into and through said upwardly directed stream of hot reducing gases passing upwardly through said upper zone of said reactor, and evolving ethylene from said feed; and producing (a) 20 to 80 grams of ethylene per 1,000 grams of dry ash-free lignite and (b) a dry char; drawing said dry char from the bottom of said reactor and drawing said ethylene from the top of said reactor with suspended solids therein, and separating said solids from said ethylene.

TABLE 1

| Proximate Analysis, % | |
| --- | --- |
| Moisture | 30 |
| Volatile Matter | 33–35 |
| Fixed Carbon | 22–29 |
| Ash | 12–13 |
| Ultimate Analysis, % | |
| Hydrogen | 5–6 |
| Carbon | 70–73 |
| Nitrogen | 1.5–1.0 |
| Oxygen | 10–23 |
| Sulfur | 1–1.3 |
| Ash | 12–13 |
| DTU/lb | 7100–7900 |

2. Process as in claim 1 wherein said fluidizing gas fed to the bottom zone comprises steam and air; the pressure in said reactor container is maintained at 5 atmospheres; said fed amounts of air and steam are added to and passed upward in said bottom zone whereat said air and steam react with and are heated by warmed decomposed solid lignite components at a nearly linear upwardly increasing temperature gradient; and wherein said heated gases pass into and through said middle high gas velocity zone of miximum temperature at a steady temperature and the resulting gases pass from said middle zone into said reactor upper zone and the gas velocity is lower in said upper zone than in said middle zone.

3. Process as in claim 1 wherein said fluidizing gas comprises 0.3 pounds of air and 0.45 pounds of steam for each pound of lignite.

4. Process of operating a reactor container and producing ethylene containing gas, said reactor container extending vertically and having near its bottom a bottom low gas velocity zone, with a fluidizing gas feed to said bottom zone, and an upper low gas velocity zone located adjacent the top of said reactor container, and, intermediate said upper and bottom zones, a middle high gas velocity maximum temperature zone and comprising steps of;

feeding a fluidizing gas feed to said bottom zone;

passing a vertically directed stream of hot reducing gases upwardly through said upper zone in said reactor container, said hot reducing gases coming from the bottom and middle zones of said reactor container;

operating said reactor with (a) linear and upwardly decreasing temperature gradient gas in said upper zone of said reactor container, (b) a linear and upwardly increasing temperature gradient gas in said bottom zone, and (c) a temperature maintained at a steady value within range of 800°–1,000° C. and a gas velocity maintained at a steady value within range of 90–180 cm. per sec. at pressures less than 7 atmospheres in said middle zone;

adding a solid feed mixture of sub-bituminous coal and solid lignite and unsaturated hydrocarbon-producing compounds and having a chemical analysis as in Table I, said feed mixture being in form of a ground mass of solid particles 80% by weight less than 0.15 centimeters in diameter, downwardly into and through said upwardly directed stream of hot reducing gases passing upwardly through said upper zone of said reactor, and evolving ethylene from said feed mixture; and producing 20 to 80 grams of ethylene per 1,000 grams of dry ash-free feed mixture and a dry char; drawing said dry char from the bottom of said reactor and drawing said ethylene from the top of said reactor with suspended solids therein, and separating said solids from said ethylene.

TABLE 1

| Proximate Analysis, % | |
| --- | --- |
| Moisture | 30 |
| Volatile Matter | 33–35 |
| Fixed Carbon | 22–29 |
| Ash | 12–13 |
| Ultimate Analysis, % | |
| Hydrogen | 5–6 |
| Carbon | 70–73 |
| Nitrogen | 1.5–1.0 |
| Oxygen | 10–23 |
| Sulfur | 1–1.3 |
| Ash | 12–13 |
| DTU/lb | 7100–7900 |

5. Process as in claim 4 wherein said hot fluidizing gas fed to the bottom zone comprises steam and air; the pressure in said reactor container is maintained at 5 atmospheres; said fed amounts of air and steam are added to and passed upward in said bottom zone whereat said air and steam react with and are heated by warmed decomposed feed mixture at a nearly linear upwardly increasing temperature gradient; and wherein said heated gases pass into and through said middle high gas velocity zone of maximum temperature at a steady temperature and the resulting gases pass from said middle zone into said reactor upper zone and the gas velocity is lower in said upper zone than in said middle zone.

6. Process as in claim 4 wherein said fluidizing gas comprises 0.3 pounds of air and 0.45 pounds of steam for each pound of solid feed mixture.

7. Process of operating a reactor and producing ethylene containing gas, said reactor container extending vertically and having near its bottom a bottom low gas velocity zone, with a fluidizing gas feed to the bottom zone and an upper low gas velocity zone located adjacent the top of said reactor container, and, intermediate said upper and lower zones, a middle high gas velocity maximum temperature zone, and comprising the steps of;

feeding a fluidizing gas feed to said bottom zone;

passing a vertically directed stream of hot reducing gases upwardly through the upper zone of said reactor container, said hot reducing gases coming from the bottom and middle zones of said reactor container;

operating said reactor with (a) a linear and upwardly decreasing temperature gradient gas in said upper zone of said reactor container, (b) a linear and upwardly increasing temperature gradient gas in said bottom zone, and (c) a temperature maintained at a steady value within range of 800°–1,000° C. and a gas velocity maintained at a steady value within range of 90–180 cm. per sec. at pressures less than 7 atmospheres in said middle zone; and adding a solid feed mixture composed of lignite, cellulose, modified cellulose and unsaturated hydrocarbon producing compounds, said feed mixture being in form of a ground mass of solid particles 80% by weight less than 0.15 centimeters in diameter, downwardly into and through said upwardly directed stream of hot reducing gases passing upwardly through said upper zone of said reactor, and evolving ethylene from said feed mixture; and producing 20 to 80 grams of ethylene per 1,000 grams of dry ash-free feed mixture and a dry char, and drawing said dry char from the bottom of said reactor and drawing said ethylene from the top of said reactor with suspended solids therein, said separating said solids from said ethylene.

8. Process as in claim 7 wherein said hot fluidizing gas fed to the bottom zone comprises steam and air; the pressure in said reactor container is maintained at 5 atmospheres; said fed amounts of air and steam are added to and passed upward in said bottom zone whereat said air and steam react with and are heated by warmed decomposed feed mixture at a nearly linear upwardly increasing temperature gradient; and wherein said heated gases pass into and through said middle high gas velocity zone of maximum temperature at a steady temperature and the resulting gases pass from said middle zone into said reactor upper zone and the gas velocity is lower in said upper zone than in said middle zone.

9. Process as in claim 7 wherein said fluidizing gas comprises 0.3 pounds of air and 0.45 pounds of steam for each pound of solid feed mixture.

* * * * *